United States Patent [19]

Kasevich et al.

[11] Patent Number: 4,776,086
[45] Date of Patent: Oct. 11, 1988

[54] METHOD AND APPARATUS FOR HYPERTHERMIA TREATMENT

[75] Inventors: Raymond S. Kasevich, Weston; James F. McQueeney, Natick; Ronald H. Crooker, Stoneham, all of Mass.

[73] Assignee: Kasevich Associates, Inc., Woburn, Mass.

[21] Appl. No.: 100,465

[22] Filed: Sep. 24, 1987

Related U.S. Application Data

[62] Division of Ser. No. 834,199, Feb. 27, 1986, Pat. No. 4,700,716.

[51] Int. Cl.⁴ .................................. H01B 13/20
[52] U.S. Cl. ........................ 29/828; 128/784; 174/75 C; 174/88 C; 333/257; 439/578; 439/585
[58] Field of Search ............. 29/828, 857; 174/75 C, 174/88 C; 128/804; 333/237, 245, 260; 439/578–585

[56] References Cited

U.S. PATENT DOCUMENTS

| | | |
|---|---|---|
| 3,230,957 | 1/1966 | Siefert et al. |
| 3,800,802 | 4/1974 | Berry et al. |
| 3,810,186 | 5/1974 | Nakahara et al. ............... 333/237 X |
| 4,138,188 | 2/1979 | Shannon ............................ 439/578 |
| 4,204,549 | 5/1980 | Paglione ........................... 128/784 |
| 4,240,445 | 12/1980 | Iskander et al. |
| 4,271,848 | 6/1981 | Turner et al. |
| 4,341,227 | 7/1982 | Turner. |
| 4,345,370 | 8/1982 | Cartier et al. .................... 29/828 |
| 4,358,764 | 11/1982 | Cheal et al. ...................... 333/237 |
| 4,374,458 | 2/1983 | Komada ........................... 174/75 E |
| 4,403,618 | 9/1983 | Turner et al. |
| 4,583,556 | 4/1986 | Hines et al. |
| 4,612,940 | 9/1985 | Kasevich et al. |
| 4,658,836 | 4/1987 | Turner. |
| 4,660,007 | 4/1987 | Edwards et al. ................. 333/237 |
| 4,662,383 | 5/1987 | Sogawa et al. .................. 128/784 |
| 4,700,716 | 10/1987 | Kasevich et al. |

FOREIGN PATENT DOCUMENTS

| | | |
|---|---|---|
| 105677 | 4/1984 | European Pat. Off. |
| 2303517 | 10/1976 | France. |
| 787043 | 12/1980 | U.S.S.R. ............................ 128/804 |

Primary Examiner—Timothy V. Eley
Assistant Examiner—Carl J. Arbes
Attorney, Agent, or Firm—Wolf, Greenfield & Sacks

[57] ABSTRACT

A microwave collinear antenna array applicator for in situ or in vivo treatment of tumors and/or other materials by hyperthermia is disclosed. The array consists of a plurality of harmonically related resonant coaxial antenna elements connected electrically in series to provide uniform heating along the entire length of the array. At the distal end of the array, a resistor may be provided at the inner conductor for steering the heating pattern. At the proximal end of the array, an impedance matching dielectric structure is provided to enable maximum power transfer to the array and to minimize stray leakage currents along the outside of the coaxial transmission line. The array may be made longer or shorter without changing frequency and therefore, depth of penetration by simply adding or subtracting half-wave resonant elements or sections of coaxial transmission line. A lossy sleeve member may be provided around the applicator to provide a localized source of heat.

8 Claims, 3 Drawing Sheets

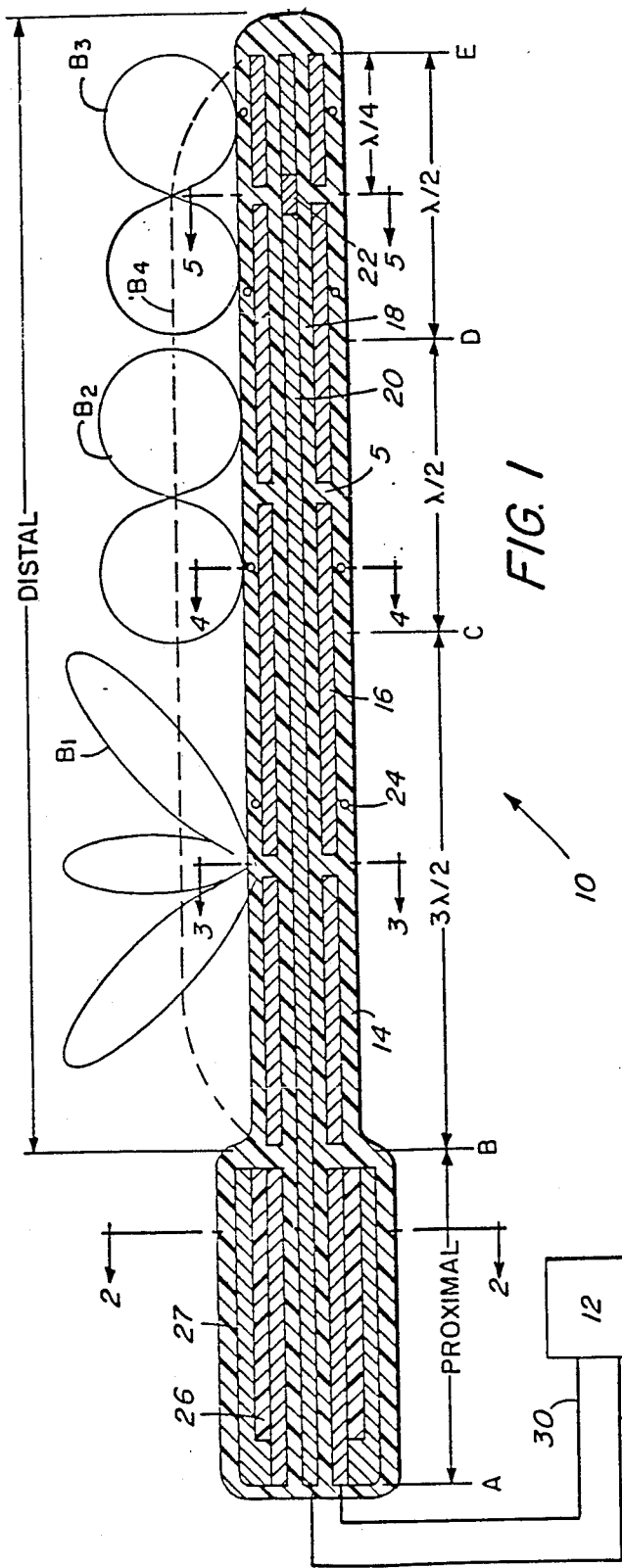
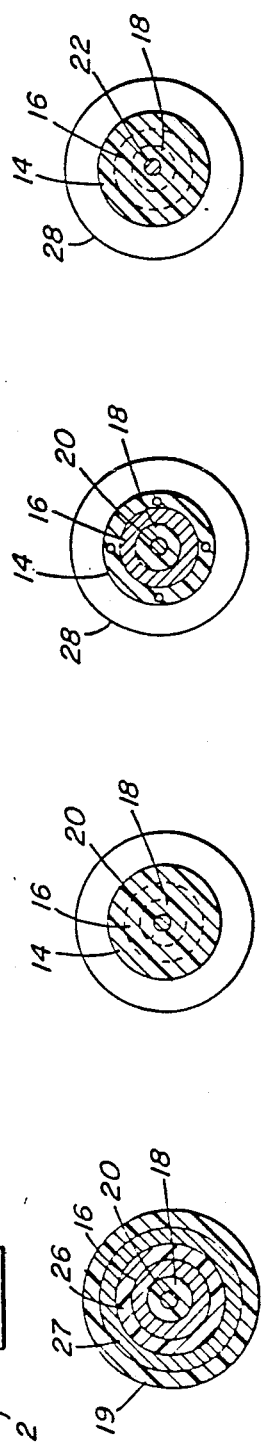

$$R_2 = \sqrt{(Z+Z')^2 + r^2} = \sqrt{R_o^2 + Z'^2 + 2R_o Z' \cos\theta}$$

$$R_1 = \sqrt{(Z-Z')^2 + r^2} = \sqrt{R_o^2 + Z'^2 - 2R_o Z' \cos\theta}$$

METHOD AND APPARATUS FOR HYPERTHERMIA TREATMENT

RELATED APPLICATION

This is a division of application Ser.No. 834,199, filed Feb. 27, 1986, and now U.S. Pat. No. 4,700,716.

TECHNICAL FIELD

This invention relates to a microwave antenna for treatment of deep seated cancerous tumors by hyperthermia and other biomedical and geological applications involving the use of dielectric heating for treatment of materials.

BACKGROUND ART

The use of elevated temperatures, i.e., hyperthermia, to repress tumors has been under continuous investigation for many years. When normal human cells are heated to 41°–43° C., DNA synthesis is reduced and respiration is depressed. At about 45° C., irreversible destruction of structure, and thus function of chromosome associated proteins, occurs. Autodigestion by the cell's digestive mechanism occurs at lower temperatures in tumor cells than in normal cells.

In addition, hyperthermia induces an inflammatory response which may also lead to tumor destruction. Cancer cells are more likely to undergo these changes at a particular temperature. This may be due to intrinsic differences, between normal cells and cancerous cells. More likely, the difference is associated with the lop pH (acidity), low oxygen content and poor nutrition in tumors as a consequence of decreased blood flow. This is confirmed by the fact that recurrence of tumors in animals, after hyperthermia, is found in the tumor margins; probably as a consequence of better blood supply to those areas.

Conventional methods of cancer treatment are surgery, radiation (X-ray) therapy and chemotherapy. In radiation therapy and chemotherapy, there are important interactions with hyperthermia. Acidity, hypoxia (low oxygen tension) and decreased nutrition all lead to increased susceptibility to hyperthermia treatment. In contrast, these conditions lead to resistance to radiation therapy and chemotherapy. Thus, hyperthermia has been suggested as an adjunct treatment to enhance the other two treatments.

The differences are fundamental. Radiotherapy chiefly affects cells in mitosis (cell division), while hyperthermia is most effective during the DNA synthesis phase. Heat impairs recovery from sublethal radiation damage. When heat and radiation are given together, or heat prior to radiation, there is thermal enhancement of radiation damage to both normal tissue and tumors. However, if radiation therapy is given prior to hyperthermia, thermal enhancement of radiation damage for tumors is greater than normal tissue.

Despite the ability to reasonably define radiation fields and the availability of accurate radiation dosimetry, damage to normal structures, which cannot be avoided, result in dose limiting factors in radiation therapy. Thus, the avoidance of significant hyperthermia to adjacent normal structures is critical for hyperthermia to become a useful adjunct to radiation therapy.

Recent clinical studies support the proposition that radiation therapy and hyperthermia can be combined effectively. In addition, both in vivo and in vitro experiments show that the effects of chemotherapy are also enhanced by hyperthermia. This enhancement may be due to increased membrane permeability at higher temperatures (drugs get into cells more easily) and inhibition of repair mechanisms for drug induced cellular damage. Since chemotherapy is given to the entire body, precise localization of hyperthermia is again essential in combination with chemotherapy to avoid significant damage to normal tissues.

A practical hyperthermia applicator must comply with the following criteria:

1. In order to treat tumors in all areas of the body, depth of penetration is essential. The major limitation to many promising hyperthermia techniques is the inability to achieve high temperatures in deep structures.

2. The applicator must have the ability to focus hyperthermia and quantitatively absorb heat in all areas of the tumor. Studies have shown that very high temperatures (approximately 50° C.) are most effective in cases where this temperature can be achieved. Methods that rely on temperature focusing, rather than on the ability of normal tissues to dissipate heat, allow these temperatures to be achieved.

3. The temperature throughout the tumor should be well-defined and uniform. The development of relative cool spots in a non-homogenous tumor may result in failure of cell kill and selection of cells with thermal tolerance (resistance to hyperthermia) within that area. Small differences in temperature may produce large differences in cell kill.

The above criteria lead to the following requirements, which, if fulfilled, will allow the accurate measurements needed to develop dose response to therapy relationships which are necessary to provide uniform treatment for all patients and evaluation of clinical studies.

1. The technique should enable induction of hyperthermia to a well-defined volume. The fall-off of temperature beyond the tumor volume should be steep.

2. The level of hyperthermia should be precisely controllable.

3. Temperature distribution within the tumor volume should be uniform at therapeutic levels.

4. It should be possible to control the heat transferred in different regions of the tumor volume.

5. The therapist and not the changing characteristics of the heated tumor should control the temperature within the tumor volume, to avoid overheating a necrotic liquefied tumor center or underheating a well vascularized growing tumor edge.

6. In addition, one should be able to accurately monitor temperature.

Applying these criteria to existing hyperthermia devices, reveals that while some devices have advantages in some areas, all have limitations. Non-invasive hyperthermia applicators, such as ultrasound and electromagnetic radiation, are easier to use than invasive techniques, but are limited in depth of penetration. Ultrasound has poor penetration in bone and air. External microwave beam heating is limited by a shallow depth of penetration and the development of standing waves, creating hot and cold spots.

Consequently, more recently, investigations have been conducted into the feasibility of using invasive applicators in the form of small diameter microwave antennas or probes as a means of producing local hyperthermia in cancerous tissue. In this form of therapy, antenna probes are inserted into the body through the esophagus or rectum, or directly into a tumor using a hollow plastic catheter.

Typically, these probes comprise a quarter-wavelength monopole antenna with frequencies in the 500 MHz to 3 GHz range. These antenna are referred to by workers in the hyperthermia field as a dipole, or a sleeve dipole. A folded back quarter wave choke forms one-half of the antenna length (S. Silver, "Microwave Antenna Theory and Design", *Dover Publication*, Chapter 8, p 241 and *Electromagnetics*, Vol. 1, No. 1, January-March 1981, p 58). The latter more nearly approximates a dipole antenna pattern.

These prior art dipole antennae suffer from a number of shortcomings, such as, poor impedance matching; high sensitivity to changes in the length of penetration of the probe into the body; poor uniformity in electric field and heating patterns produced; and lack of beam steering and heat sensing capabilities. J. W. Strohbehn, et al., "An Invasive Microwave Antenna for Locally-Induced Hyperthermia for Cancer Therapy", *Journal of Microwave Power*, 14 (4), 1979, pp 339-350; D. C. de-Sieyes, et al., "Optimization of an Invasive Microwave Antenna for Local Hyperthermia Treatment of Cancer", *Thayer School of Engineering*, Dartmouth College, July 7, 1980; J. W. Strohbehn, et al., "Evaluation of an Invasive Microwave Antenna System for Heating Deep-Seated Tumors", presented at the *Third International Symposium: Cancer Therapy by Hyperthermia, Drugs and Radiation*, Fort Collins, Colorado, June 22-26, 1980.

DISCLOSURE OF THE INVENTION

The invention comprises an invasive hyperthermia applicator for generating a well-defined uniform pattern of electromagnetic radiation, preferably in the microwave frequency spectrum of 500 megahertz to 5 gigahertz, to produce well-defined temperatures throughout a tumor. The applicator is in the form of an elongate tubular member forming a collinear array of antennae fabricated from a common coaxial transmission line. In the preferred embodiment of the invention, a plurality of antennae, i.e., three, are formed from the coaxial transmission line by forming circumferential gaps in the outer conductor of the transmission line.

These gaps serve as antenna feeds for subsequent antenna elements. The applicator has a proximal section and a distal section. The three collinear antennas are located in the distal section and a coaxial impedance matching transformer is provided in the proximal section in the form of a circumferential volume of dielectric material with a conductor external to the outer coaxial line.

Progressing from the proximal section to the distal section, a first three half wavelength collinear antenna is provided. Then, two half wavelength antennas are provided, which are harmonically related to the three half wavelength antenna. The combined near field radiation pattern of the three antenna array produces a uniform temperature pattern along the distal section of the applicator at a frequency which produces a minimum in the reflected power inside the coaxial transmission line.

The circumferential gaps in the outer conductor of the transmission line result in a voltage being generated across the gap. The gap voltage excites antenna currents that flow on the outer conductor of the transmission line through the center conductor, continues down the line to the next feed gap. The gaps thereby result in a radiation aperture. Preferably, the gap spacings from the distal end of the array are multiples of one-half of the antenna current wavelength. A standing wave of antenna current develops along the entire distal end of the array.

An outer plastic sheet or coating of dielectric material is provided around the collinear array, which may optionally include embedded therein, fiber optic sensor bundles, for measuring the temperature at the delivery site.

Optionally, a sleeve of lossy, i.e., electromagnetic energy absorbing material, such as ferrite, may be disposed around the outer plastic sheet or coating at a predetermined location or locations along the distal length of the antenna array. Some of the electromagentic energy radiated by the antenna is strongly absorbed by the ferrite sleeve which becomes hot and provides a source of localized heat for heating a tumor site. This heat source is independent of the electromagnetic energy absorbing properties of the tumor and produces hyperthermia range temperatures with significantly less power input than purely electromagnetic energy radiation permits. This sleeve tends to diminish the severity of the temperature gradient close to the antenna and thus permits more uniform temperatures near the antenna.

BRIEF DESCRIPTION OF THE DRAWINGS

FIG. 1 is a cross-sectional view of the applicator of the present invention showing in solid lines a cross-section of one-half of the far field antenna array pattern resulting from each of the three antenna elements and in dotted lines the near field heating pattern resulting from the super position of the electromagnetic energy pattern generated by the three antenna elements.

FIG. 2 is a cross-sectional view through the applicator 10 of FIG. 1 along the lines 2—2.

FIG. 3 is a cross-sectional view of the applicator of FIG. 1 along the lines 3—3.

FIG. 4 is a cross-sectional view of the applicatior of FIG. 1 along the lines 4—4.

FIG. 5 is a cross sectional view of the appliator of FIG. 1 taken along lines 5—5.

BEST MODE OF CARRYING OUT THE INVENTION

I. APPLICATOR

Figure 6:
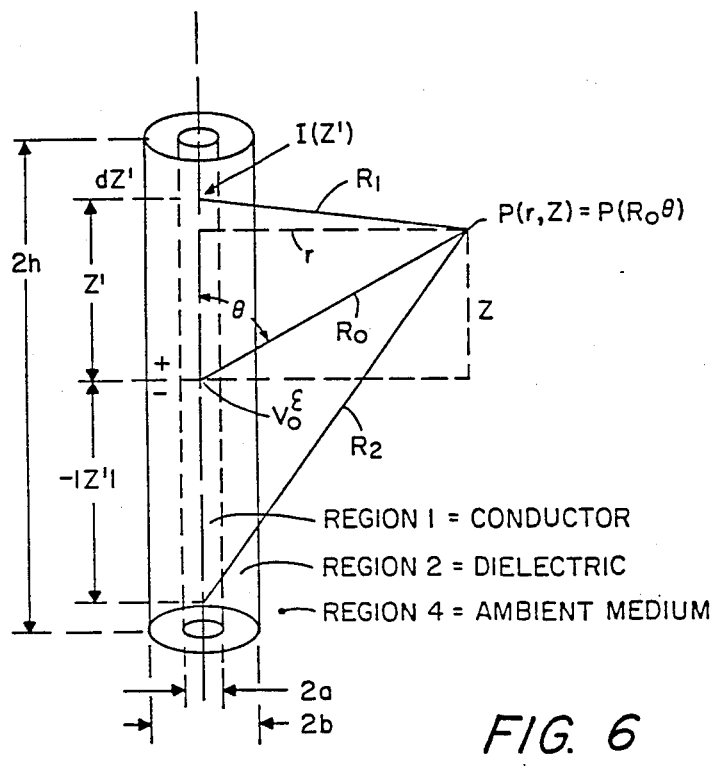
FIG. 6 is an illustration of an insulated dipole in an ambient medium used to depict the algebraic parameters needed for calculating the optimum transformer parameters.

Referring to FIGS. 1-4, the invention will now be described in detail in connection therewith. An applicator 10, for uniform heating of a tumor with well defined temperatures throughout the tumor and without hot spots either within or outside the tumor volume, is shown in the form of a collinear array of three antennae fabricated from a coaxial transmission line comprising inner conductor 20 and outer coaxial conductor 16 with an impedance matching element at the array proximal end.

The three antennae are formed by providing circumferential gaps 5 in the outer conductor 16 to expose the dielectric core 18 of the transmission line structure. Preferably, the widths of the gaps 5 are about the same size as the distance between center conductor 20 and outer conductor 16. Core 18 may comprise a suitable solid dielectric insulator, such as PTF (polytetrafluoroethylene). The gaps 5 provide excitation feeds for more remote, i.e., more distal end, antenna sections and result in the equivalent of more than one antenna pattern being generated from the length of the center conductor. The electrical lengths of these antenna sections are harmonically related to each other.

A dielectric outer envelope 14, containing fiber optic sensors 24, extends over the outer surface of the applicator 10. For antenna beam steering purposes, a resistor 22 is provided at the longitudinal axis of the applicator. In accordance with the theoretical and experimental teaching of Altschuler ("The Traveling-Wave Linear Antenna", E. E. Altschuler, Cruft Laboratory, Harvard University, Cambridge, Massachusetts *Scientific Report No. 7*, May 5, 1960), an essentially traveling-wave distribution of current can be produced on a linear antenna by inserting a resistance of suitable magnitude one-quarter wavelenth from the end of the antenna. As shown in FIG. 21 from the above-cited reference, the effect of such resistance is to significantly change the radiation pattern of the antenna and therefore, in the present application, its heating pattern for hyperthermia. The collinear array applicator 10 of the present invention is therefore provided with the appropriate value of resistance about one-quarter wavelength from the end of the distal section. By changing the applied frequency, or the location of the resistor, the distribution of heat around the applicator may therefore be changed or "steered" in many directions.

At the proximal end of the antenna array 10, a coaxial impedance matching transformer is provided in the form of a dielectric cylinder 26 concentric with and external to the outer conductor 16. The dielectric cylinder 26 is covered with a metallic (cylindrical, layer 27 which is electrically shorted to outer conductor 16 at proximal end A. A dielectric outer envelope 14 extends over the full length of cylinder 27 and distal section B-E. The transformer minimized the reflected power within the feed transmission line and also prevents leakage of antenna curents along the outside of the array applicator 10. By judicious selection of operating parameters, both functions (minimizing reflected power and leakage prevention) occur at approximately the same operating frequency. The operating parameters of the coaxial impedance matching transformer are based on the theoretical equations developed by R. W. P. King, "The Electromagnetic Field of an Insulated Antenna in a Conducting or Dielectric Medium", R. W. P. King et al., *IEEE Transactions on Microwave Theory and Techniques*, Vol. MIT-31, No. 7, July 1983.

The transformer provides a load impedance at the proximal end of the collinear arrays for R.F. power coupled from source 12 via lines 30 and 32 across the inner and outer conductors 20 and 16. This load impedance regulates the antenna current at the feed points or gaps 5 to more nearly match the 50 ohm impedance of the feed transmission line 30 and 32 with the input impedances of the collinear array 10. The distal section of applicator 10 of FIG. 1 has an overall length B-E of 10 centimeters at a frequency of 915 megahertz. This length is a multiple of one-half of the wavelength of the input frequency, (i.e. 5, $\lambda_L/2$ sections) and is physically represented by a full-wave linear antenna (C-E) series connected to a three halves wave linear antenna (B-C). This arrangement of antennae provides a uniform heating pattern shown in the dotted lines labelled B4 of FIG. 1.

Note that heating pattern B4 is one-half of a plane cut through the full cylindrical near field heating pattern extending from array 10, which is related to the superposition of the three individual far field antenna patterns, B1, B2 and B3, shown in solid lines. If a shorter antenna array is desired, the frequency may be doubled and the length halved. Alternatively, for the same frequency, section C-D can be removed to reduce the length to 8 cm or section B-C can be removed to reduce the length to 4 cm.

II. THEORY OF OPERATION

In operation, as the transmitted power from source 12 flows down the coaxial line, formed by inner and outer conductors 20 and 16 separated by dielectric 18, voltage excites each antenna section and electromagnetic energy is radiated from the applicator which is absorbed by the lossy tissue. The absorbed energy reduces the amplitude of the transmitted power. By increasing the number of elements at the distal end of the array (and decreasing the spacing between elements), a higher sectional antenna gain is achieved, as compared to the more proximal section B-C, which will have a lower gain because it is a single $(3\lambda/2)$ element.

More specifically, the square of the electric field for the half-wavelength (1), full wavelength linear (2) and 3/2 wavelength (3), antennas in free space, shown below, provides an indication of the radiated power distribution for the collinear array in lossy material (J. D. Jackson, "Classical Electrodynamics", J. Wiley, 1975, Second Edition, pps 402–403):

$$\text{For } \frac{\lambda}{2} \text{ Antenna: } E^2 \alpha \frac{\cos^2\left(\frac{\pi}{2}\cos\Theta\right)}{\sin^2\Theta} \quad (1)$$

$$\text{For } \lambda \text{ Antenna: } E^2 \alpha \frac{4\cos^4\left(\frac{\pi}{2}\cos\Theta\right)}{\sin^2\Theta} \quad (2)$$

$$\text{For } \frac{3\lambda}{2} \text{ Antenna: } E^2 \alpha \frac{\cos^2(3\pi/2\cos\Theta)}{\sin^2\Theta} \quad (3)$$

wherein $\theta$ is measured from the longitudinal axis of the antenna.

The full wave antenna, distribution (C-E) can be considered as resulting from the coherent superposition of the fields of two collinearly adjacent half-wave antennae patterns $B_2$ and $B_3$ excited in phase; the power intensity at $\theta = \pi/2$ is 4 times that of half-wave length antenna. Thus, the extreme distal section (C-E) of two series connected half wave antennas radiates 6 dB more power per solid angle than the three half wave length section (B-C). Based on geometric reasoning, the total power radiated by the three half wave length antenna is about 60% of the total power delivered to the array (6 cm length compared with 4 cm length). Therefore, forty percent is left over for radiation by the series connected half wave antennae (C-F). The 6 dB gain of the $3\lambda/2$ section compensates for this loss. The result is a nearly uniform heating pattern along the entire 10 cm length of distal section B-E of array applicator 10.

III. MANUFACTURING PROCESS

Preferably, the collinear array applicator 10 is fabricated using standard AWG (American Wire Gauge) solid or stranded tin plated copper wire (AWG 26 for example) for inner conductor 20. The existing insulation of the copper wire may be increased in diameter by means of a thin wall plastic tube of PTF to form core 18. The outer surface of the tube or core 18 is coated with a conductive ink or paint, such as silver, to provide the outer conductor 16 of a two conductor 50 ohm transmission line system. Etching of the tube may be required to insure adhesion of the silver paint. The gap location 5 are not covered with the conductive ink because they are masked off during the paint application process. A uniform PTF coating 14 is then applied over the entire distal section B-E. The proximal section A-B is formed in a similar manner, except that prior to application of coating 14, a dielectric sleeve or coating 26 of appropriate dielectric constant and loss tangent, is placed around the conductive ink 16 located at the proximal section, The dielectric material may preferably be polyacrylamide (See "The Polyacrylamide as a Phantom Material for Electromagnetic Hyperthermia Studies", M. G. Bini, et al., *IEEE Transactions of Biomedical Engineering*, Vol. BMD-31, No. 3, March 1984) from which the appropriate dielectric constant may be calculated for the proper transformer operation using the criterion that the complex propagation constant, $k_L$ of the transformer dielectric is the same as the $k_L$ of the distal section. A uniform silver ink coating is then applied over the polyacrylamide material to form a second conductive layer 27. This second conductive layer 27 is present only over the length of the proximal section. It is applied in a manner to create a short circuit to the silver ink outer conductor 16 at proximal end A but leaves an open circuit between it and the outer conductor 16 at point B. The outer PTF coating 14 is then applied over the proximal section A-B or continued from the distal section.

This coating 14 permits the probe to operate within wide limits of variations of temperature, tissue dielectric constant and electrical conductivity. A 10 mil thick coating of PTF permits the array to maintain a constant heating pattern (ignoring the effects of heat loss or gain by conduction or convection) for a change in the dielectric constant of tissue from 30 to 80 which may occur during heat application.

Within the dielectric coating 14, fiberoptic thermometry sensors 24 may be embedded. A sensor, such as produced by the Luxtron Corporation ("16 -Channel Fiberoptic Thermometry System with Multisensor Arrays for Thermal Mapping", Wickersheim et al.) may be appropriately modified for application to the array 10. Several linear phosphor sensors 24 about 0.25 mm in diameter (10 mils) may be embedded in the outer dielectric 14. The phosphor sensors 24 utilize the temperature dependence of the fluorescent decay time of the phosphor to determine temperature.

This technique yields a simple, cost-effective multichannel system, which can support a number of small-diameter multi-sensor arrays.

IV. LOAD IMPEDANCE/TRANSFORMER LENGTH AND DIELECTRIC CONSTANT

To determine the required value of the load impedance, the proper length of the transformer and its dielectric constant are theoretically determined from the complex propagation constant $k_L$ associated with the current on the antenna, in the manner described below in connection with FIG. 6.

Consider a simple insulated dipole, FIG. 6, consisting of a central conductor (Region 1) with the half-length "h" and radius "a" surrounded by a cylinder of dielectric which may consist of one (Region 2) or two layers (Region 3)*, with the outer radii "b" and "c", respectively. Outside this insulating sheath is the infinite ambient medium (Region 4) which is a lossy or dielectric. The central conductor is sufficiently highly conducting to be well approximated by a perfect conductor. The wavenumbers of the dielectric layers are:

$$k_2 = \omega(\mu_0 \epsilon_2)^{\frac{1}{2}} \text{ and } k_3 = (\omega_0 \epsilon_3)^{\frac{1}{2}},$$

where $\epsilon_2$ and $\epsilon_3$ are the relative dielectric constants of regions 2 and 3, respectively, and are taken to be real since the dielectrics actually used are highly nonconducting and $\mu$ = relative permeability of free space and $\omega$ = the radian frequency. The wave number of the lossy dielectric ambient medium is:

$$k_4 = \beta_4 + i\alpha_4 = \omega(\mu_0 \epsilon_4)^{\frac{1}{2}}, \; \epsilon_4 = \epsilon_4 + i\sigma_4/\omega;$$

wherein $\beta$ = the phase constant in radians/meter;

$\alpha$ = the attenuation constant in Nepers/meter and $\sigma$ = the electrical conductivity in Siemens/meter.

*For simplicity only Region 2 is shown in FIG. 6

The general theory of the insulated antenna applies when the wavenumber of the ambient medium is large compared to that of the insulating sheath and the cross-section of the antenna is electrically small. That is $$|k_4/k_2|^2 >> 1; \; |k_4/k_3|^2 >> 1; \; (k_2b)^2 >> 1; \quad (1)$$
$$(k_3c)^2 >> 1.$$

Subject to these conditions and with the time dependence $e^{-i\omega t}$, the current in the central conductor is $$I(z) = I(0) \frac{\sin k_L(h - |z|)}{\sin k_L h} \quad (2a)$$

$$I(0) = V_o^e Y_o = V_o^e / Z_o$$

where admittance is:

$$Y_o = -(i/2Z_c)\tan k_L h. \quad (2b)$$

For a dielectric with two layers:

$$k_L = k_2 \left[ \frac{\ln(c/a)}{\ln(b/a) + n_{23}^2 \ln(c/b)} \right]^{\frac{1}{2}} \left[ \frac{\ln(c/a) + F}{\ln(c/a) + n_{24}^2 F} \right]^{\frac{1}{2}} \quad (3)$$

$$Z_c = (\omega \mu_0 k_L / 2\pi k_2^2) [\ln(b/a) + n_{23}^2 \ln(c/b) + n_{24}^2 F] \quad (4)$$

where $n_{23}^2 = k_2^2/k_3^2$, $n_{24}^2 = k_2^2/k_4^2$, and $F = H_o^{(1)}(k_4c)/k_4cH_1^{(1)}(k_4c)$; wherein $H_o^{(1)}(k_4c)$ and $H_1^{(1)}(k_4c)$ are zero and first order Hankel functions of the first kind.

These formulas can be simplified by the introduction of an effective wavenumber $K_{2e}$ and an effective permittivity $\epsilon_{2e}$ for an equivalent dielectric composed of a single layer with the outer radius c, viz, $$k_{2e} = k_2 \left[ \frac{\ln(c/a)}{\ln(b/a) + n_{23}^2 \ln(c/b)} \right]^{\frac{1}{2}} \quad (5)$$

$$\epsilon_{2e} = 2 \left[ \frac{\ln(c/a)}{\ln(b + a) + n_{23}^2 \ln(c/b)} \right]^{\frac{1}{2}}$$

With (5), the above formulas become $$k_L = k_{2e} [ln(c/a) + F]^{\frac{1}{2}} [ln(c/a) + n_2{}^2{}_4 F]^{-\frac{1}{2}} \quad (6)$$

$$Z_c = (\mu_0 k_L / 2\pi k_2{}^2) [ln(c/a) + n{}^2{}_4 F] \quad (7)$$

where $n_{2e4}{}^2 = k_{2e}{}^2 / k_4{}^2$.

Equation (3) is the complex wave number for current on the surface of cylindrical structures embedded in electrically lossy media, such as tumors. The input impedance of the bifurcated coaxial line matching transformer is given on page 59 of "Embedded Insulated Antennas for Communication and Heating" by R. W. P. King et al., *Electromagnetics*, Vol. 1, Number 1, January-March 1981. The phase constant of the dielectric inside the transformer must match with $\beta_L$ and $\beta_L d \simeq \pi/2$ gives the required length of the transformer. $\beta_L$ is the real part of $k_L$ of Equation 6. The transformer length is the length of the proximal section. Proper impedance matching of the collinear antenna array is therefore dependent on the value of $k_L$. For the proper choice of dielectric inside the transformer and length of transformer, a high value of impedance will exist at the input (Section B). This will effectively isolate the array from the feed line, and with the proper location of the input of the transformer from gap 5, give a collinear array which is properly matched to the 50 ohm feed line.

Figure 7:
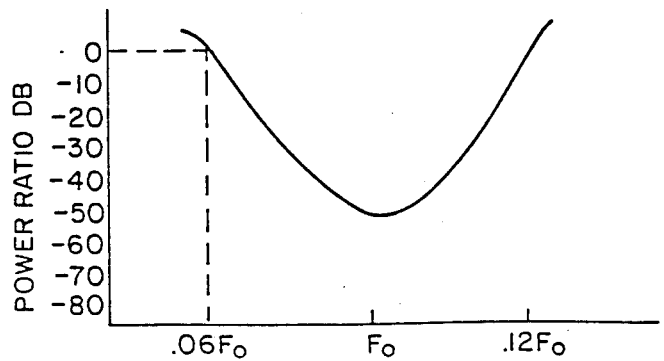
FIG. 7 is a plot of frequency versus power ratio in decibels for the applicator of the invention.

FIG. 7 shows the ratio of reflected power ($P_r$) to transmitted power ($P_t$) in decibels in the coaxial line for a 10 cm long, 3 gap, collinear array of 2 millimeter diameter made in accordance with the invention. The frequence fo is the frequency which yields the highest value of terminating impedance for the array wherein the elements of the array are harmonically related. For the 10 cm device in the example, the collinear array that achieves the uniform heating pattern consists of the elements depicted in the distal section B-E of FIG. 1, wherein the frequency is 915 megahertz. The transformer length is about 1 centimeter with a PTF dielectric inside the transformer, having a dielectric constant of 40.

Figure 8:
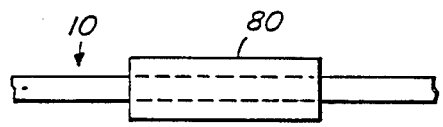
FIG. 8 is a side view of an optional embodiment of the invention wherein a lossy sleeve 80 is provided over a selected portion of the applicator.

As shown in the optional embodiment of FIG. 8, a lossy sleeve 80 comprised of ferrite cores or beads formed in the shape of a cylinder with an inner bore may be disposed about the applicator 10 at the distal end thereof. Preferably, the inner diameter of the bore in sleeve 80 forms a press fit with the outer diameter of the applicator 10 and is held inplace along the longitudinal length of the applicator by a suitable adhesive or other means. The sleeve may be used to modify the heat distribution near and around the applicator 10. We have found that by placing ferrite sleeves 80 around the antenna 10, a significant increase in heat close to the antenna and adjacent to the sleeve is produced for the same power level into the collinear antenna array applicator 10 as compared to an applicator without the sleeve. The electromagnetic fields generated by the antenna applicator 10 produce currents in the ferrite material of sleeve 80 and the resultant heat is transferred by conduction to the surrounding tumor. Significantly less input power to create hyperthermia range temperatures near the applicator (40°–44.5° C.) is required (1-2 watts as compared to 5 watts). The ferrite sleeve 80 therefore creates a source of heat for the tumor that is not dependent on the electrical properties of the tumor. Use of this sleeve provides a source of highly localized heat without requiring an electromagnetic energy absorption capability of tissue. The sleeve may also be used in conjunction with electromagnetic power dissipation in tissue to provide complex heat distribution patterns that conform to the tumor geometry. The Curie temperature of ferrite material determines the upper temperatures beyond which the material becomes non-magnetic and hence non-lossy./By selecting an appropriate Curie temperature for the ferrite sleeve, an upper limit on the temperature produced by the sleeve can be established.

Figure 10:
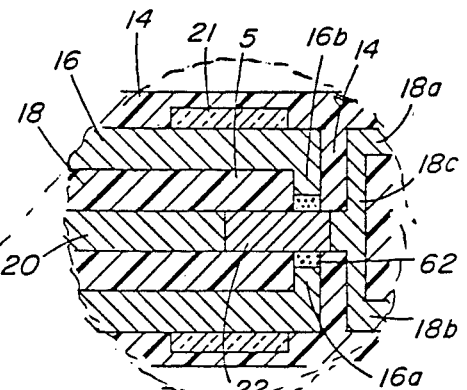
FIG. 10 is an enlarged fragmented view of FIG. 9.
Figure 9:
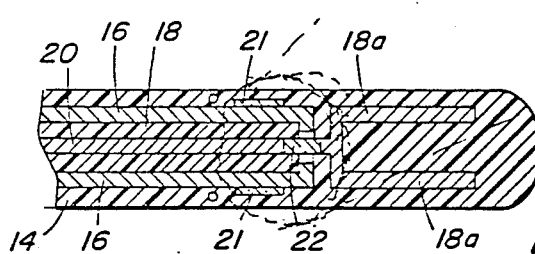
FIG. 9 is a cross-sectional view of an alternate embodiment of the outermost end of the applicator 10 of FIG. 1.

An alternate embodiment for the extreme distal end of the applicator is shown in FIGS. 9 and 10 wherein like items in FIG. 1 retain their numeral reference in FIGS. 9 and 10. As may be seen more clearly in FIG. 10, in this embodiment, the outer conductor 16 of the antenna array is terminated by a radially inwardly extending ring shown as section 16a and 16b. A beam steering resistor 22 may be disposed along the longitudinal axis of the antenna in the path of inner conductor 20, as shown Alternatively, an eguivalent beam steering resistor 21 may be formed as a circular ring embedded in outer insulator 14.

The inner walls of ring sections 16a and 16b are insulated from resistor 22 or (in the event resistor 22 is not present) from inner conductor 20 by dielectric disk 62. The inner conductor is extended radially from the longitudinal axis by disk-like conductor member 18c which is integral with coaxial conductor 18a encased in dielectric 14.

V. FLEXIBLE COAXIAL CONNECTOR

Figure 11:
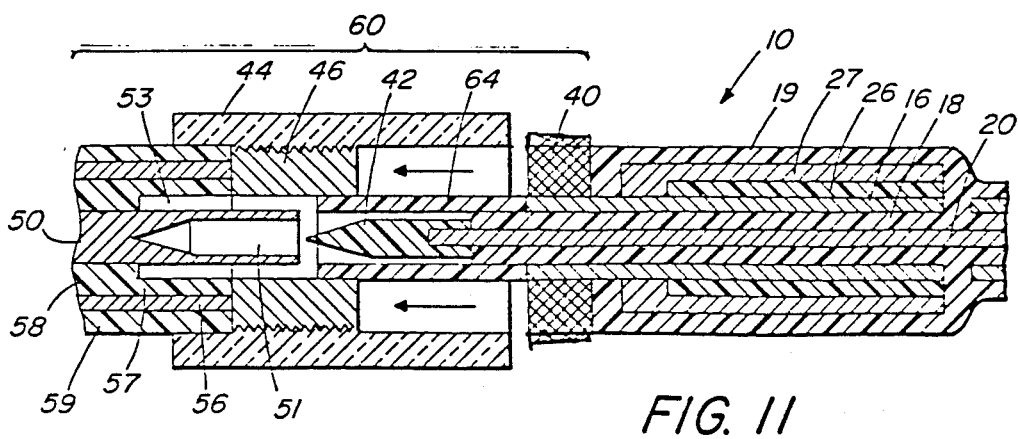
FIG. 11 is a cross-sectional exploded view of a flexible coaxial connector adaptor system 60 for use with the applicator of FIG. 1 shown in the process of being assembled.

The collinear applicator array 10 may be connected to a commercially available coaxial cable, as shown in FIG. 11, by means of a flexible coaxial connector adaptor 60. This type of connector will eliminate the need of using expensive commercially available SMA connectors. In addition, the size of SMA connectors may be excessive in diameter for certain applicaton, thereby creating the need of a special connector whose diameter will conform to the diameter of the collinear applicator.

As shown in FIG. 11, the adaptor comprises a laminated metal conductive ring 40 or ferrule having an inner diameter conforming to the outer diameter of the outer conductor 16 of applicator 10 affixed around the outer conductor. The outer conductor 16, dielectric core 18 and inner conductor 20 of applicator 10 is allowed to extend longitudinally outward from the proximal end of the applicator, with the core 18 extending beyond the outer conductor 16 and the inner conductor 20 extending beyond the core 18. An insulative sleeve 64 is affixed around the extension of core 18. An adaptor pin 42 is secured around the extension of inner conductor 20 to provide an enlarged transition from the outer diameter of inner conductor 20 to the outer diameter of standard coaxial cable inner conductors. For example, the O.D. of inner conductor 20 is preferably about 0.010 inches, the O.D. of pin 42 is 0.018 inches and the O.D. of sleeve 64 is 0.050 inches.

Pin 42 is adapted to be inserted into tapered bore 51 formed within the inner conductor 50 of a standard SMA cable inner conductor having an O.D. of 0.045 inches.

Dielectric insulator sleeve 64 is adapted to extend into coaxial channel 53 around inner conductor 50. The metal connector shell of the standard coaxial line slides over sleeve 64 and abuts ring 40. Conductive plastic elastomeric extrusion 44 is bonded at one end by conductive epoxy to shell 46 and is held to ring 40 by friction.

CLINICAL UTILIZATION

The applicator of the invention can be made as described above with an outer diameter of about 0.050 inches. With this small diameter, it can be placed almost anywhere within a patient, with or without fiber optics, using current techniques and equipment, such as endoscopes, CT scanners, ultrasound imaging systems, and fluoroscopy units.

For example, in the hyperthermia treatment of urinary tract problems. Access to this anatomic system for placement of the applicator could be obtained by any one of the following commonly practiced procedures:

1. Angiographic techniques for access to arterial or venous components (using fluoroscopy);
2. Endoscopic techniques for access to the urethera, prostate, bladder, ureters, and renal pelvis via retrograde cannulation (using fiber optic endoscopy, i.e., cyrtoscopes);
3. Percutaneous techniques for direct access by way of so-called antegrade nonsurgical approach through the flank or back to the renal pelvis; ureter and bladder (using CT, ultrasound, fluoroscopic or even endourologic equipment).

The currently available state-of-the-art imaging equipment (particularly ultrasound and CT) allows visualization and direct puncture of masses in the neck, abdomen, pelvis, and extremities. Under ultrasonic or CT guidance, long, small diameter needles (18–23 gauge) are easily introduced through the skin and into superficial or deep lesions. In a similar manner, the applicator probe 10 could be easily introduced into these lesions through any number of widely available biopsy needles.

The same techniques and equipment can be used for the relatively non-invasive (i.e., non-surgical) access and treatment of other anatomical sites. For example, the gastrointestinal tract, specifically, the biliary system, is routinely approached by endoscopic means (ERCP-endoscopic retrograde cannulation of the pancreas), as well as percutaneously by direct intercostal puncture and catherization of the liver and bile ducts for diagnosis and treatment of malignant and benign obstructions (due to hepatic, biliary, pancreatic, and lymph node diseases). Other lesions of the GI tract, such as in the stomach are now approached through gastroscopy. The relatively large size of the endoscope easily allows passage of a probe of the present size.

The small OD size of this probe, moreover, lends itself to intraoperative use, as is now being performed with small ultrasound probes in certain neurosurgical procedures.

Brain tumors are a potential area for application of the present probe in which hyperthermia may be able to play an immediate and important role. Brain tumors are frequent in the population and histiological types with extremely poor prognosis can be identified. Failure to control local disease and not distant metastasis is by far the major cause of mortality, and clinical trials may be initiated with patients who have failed other modalities (surgery, radiation therapy, chemotherapy). In addition, relatively non-invasive techniques (such as through a burr hole) to guide placement and to monitor results are applicable. The lossy sleeve embodiment of FIG. 8 is capables of use for dissolving arterial plaque specifically for use in angiosurgery.

This completes the description of the preferred 10 embodiment of the invention.

Equivalents

While the particular embodiment above described has been concerned mainly with the application of hyperthermia for treatment of cancerous tumors in situ humans or animals, it also may find application in treatment of materials, such as oil shales, tar sands, coal tar and the like. Hence, the invention is not to be construed as limited to the particular embodiment shown and described herein. There are many equivalents to these specific embodiments and such equivalents are intended to be covered by the following claims.

What is claimed is:

1. The method of forming a small diameter electromagnetic radiation applicator having a distal section and a proximal section and comprised of an inner conductor and an outer coaxial conductor comprising the steps of:
   (a) forming a dielectric inner core layer around the inner conductor;
   (b) masking radial strips about the periphery of the dielectric layer at harmonically related distances along the length of said inner conductor at the distal section thereof;
   (c) coating the unmasked portions of the dielectric layer with a thin metallic conductive layer to form said outer coaxial conductor;
   (d) forming an impedance matching transformer at the proximal section; and
   (e) forming a protective dielectric sheath layer ovor the distal and proximal sections.

2. The method of claim 1 wherein the transformer is formed by:
   (f) coating the proximal section after step (c) with an impedance matching layer of dielectric material, matched to the dielectric constant of the media in which the applicator will be used; and
   (g) forming a metallic tubular layer over said impedance matching layer in contact at one end with said outer coaxial conductor.

3. The method of claim 2 wherein said impedance matching layer is formed of polyacrylamide.

4. The method of claim 1 wherein the masking strips are three in number and are located respectively one-quarter wavelength, three-quarter wavelength, and five-quarter wavelength from the distal end of the inner conductor.

5. The method of claim 1 wherein the frequency of the radiation is about 915 megahertz, the length of the transformer is about 1 centimeter and the length of the distal section is about 10 centimeters.

6. The method of claim 1 wherein fiberoptic thermometry sensors are embedded in the sheath layer.

7. The method of claim 2 wherein the metallic layer is formed of silver.

8. An adaptor for coupling the inner and outer conductors of small diameter coaxial line microwave hyperthermia applicators to larger diameter standard coaxial line cables wherein said inner and outer conductors are separated by a dielectric core, comprising:

(a) a transition pin adapted to fit over an extension of inner conductor for insertion into the inner conductor of the standard cable;
(b) an insulative sleeve fitted over an extension of said core with a grooved space formed between said sleeve and said pin;
(c) a metallic conductive ring affixed around the outer conductor over an extension thereof which abuts said sleeve; and
(d) an elastomeric conductive sleeve retaining member adapted to fit around the outer portion of said standard cable and said ring for retaining said applicator and cable in interlocking relationship.

* * * * *

UNITED STATES PATENT AND TRADEMARK OFFICE
CERTIFICATE OF CORRECTION

PATENT NO. : 4,776,086

DATED : October 11, 1988

INVENTOR(S) : Raymond S. Kasevich et al

It is certified that error appears in the above—identified patent and that said Letters Patent is hereby corrected as shown below:

Column 4, line 39, "applicatior" should be --applicator--.

Column 4, line 41, "appliator" should be --applicator--.

Column 5, lines 13-14, "polytetrafluorethylene" should be --polytetrafluoroethylene--.

Column 5, line 47, "(cylindrical," should be --(cylindrical)--.

Column 8, lines 42-43, "$(k_2b)^2>>1; (k_3c)^2>>1.$" should be --$(k_2b)^2<<1; (k_3c)^2<<1.$--

Column 9, line 46, "frequence fo" should be --frequency fo--.

Column 9, line 63, "inplace" should be --in place--.

Column 10, line 33, "shown" should be --shown.--.

Column 10, line 33, "eguivalent" should be --equivalent--.

Column 11, line 58, "catherization" should be --catheterization--.

UNITED STATES PATENT AND TRADEMARK OFFICE
CERTIFICATE OF CORRECTION

PATENT NO. : 4,776,086

DATED : October 11, 1988

INVENTOR(S) : Raymond S. Kasevich et al

It is certified that error appears in the above-identified patent and that said Letters Patent is hereby corrected as shown below:

Column 12, line 13, "capables" should be --capable--.

Column 12, line 47 (claim 1), "ovor" should be --over--.

Signed and Sealed this

Thirteenth Day of June, 1989

Attest:

DONALD J. QUIGG

*Attesting Officer*     Commissioner of Patents and Trademarks